United States Patent
Feng et al.

(10) Patent No.: US 7,524,889 B2
(45) Date of Patent: Apr. 28, 2009

(54) LIGHT EMITTING DIODE CURABLE ACRYLATES WITH REDUCED YELLOWING

(75) Inventors: Li Feng, Naperville, IL (US); Byoung I. Suh, Oak Brook, IL (US)

(73) Assignee: Bisco, Inc., Schaumburg, IL (US)

( * ) Notice: Subject to any disclaimer, the term of this patent is extended or adjusted under 35 U.S.C. 154(b) by 129 days.

(21) Appl. No.: 11/481,544

(22) Filed: Jul. 6, 2006

(65) Prior Publication Data

US 2008/0009557 A1   Jan. 10, 2008

(51) Int. Cl.
*C08F 2/48* (2006.01)
*C08F 2/50* (2006.01)
*A61K 6/00* (2006.01)
*A61K 6/083* (2006.01)

(52) U.S. Cl. .............................. 522/2; 522/25; 522/48; 522/182; 522/173; 522/28; 522/64; 522/183; 523/116; 433/228.1

(58) Field of Classification Search .................... 522/25, 522/28, 182, 48, 2, 173, 183; 433/228.1; 523/116
See application file for complete search history.

(56) References Cited

U.S. PATENT DOCUMENTS

| | | | | |
|---|---|---|---|---|
| 5,750,590 | A  * | 5/1998 | Schaefer et al. | 523/115 |
| 5,980,253 | A  * | 11/1999 | Oxman et al. | 433/228.1 |
| 6,458,865 | B2 * | 10/2002 | Chappelow et al. | 522/14 |
| 6,468,077 | B1 * | 10/2002 | Melikechi et al. | 433/29 |
| 6,596,445 | B1 * | 7/2003 | Matsumoto et al. | 430/7 |
| 6,747,071 | B1 * | 6/2004 | Frances | 522/148 |
| 6,818,679 | B2 * | 11/2004 | Fukushima et al. | 522/64 |
| 7,081,485 | B2 * | 7/2006 | Suh et al. | 522/28 |
| 2005/0154081 | A1* | 7/2005 | Yin et al. | 523/115 |

* cited by examiner

*Primary Examiner*—Susan W Berman
(74) *Attorney, Agent, or Firm*—Homer W. Faucett, III; Richard A. Schnurr; Ice Miller LLP

(57) ABSTRACT

Dental compositions and methods of curing the composition utilizing a light emitting diode (LED) curing unit. According to one aspect, a composition comprising a multiacrylate compound, an initiator including camphorquinone and at least one amine, and a colorless anti-yellowing agent produces a scratch free surface having no oxygen inhibited layer when cured with the LED curing unit.

28 Claims, No Drawings

LIGHT EMITTING DIODE CURABLE ACRYLATES WITH REDUCED YELLOWING

BACKGROUND

The invention relates to dental compositions, and more specifically, to polymerizable dental compositions, and more specifically to polymerizable dental compositions containing multifunctional acrylate compounds that are polymerizable by use of a light emitting diode ("LED") and other light sources, and cure without an oxygen inhibited layer, and with reduced or no unwanted yellow cast. In general, dental sealants and adhesives are widely used in clinical settings. Desirable properties include safety, efficacy, durability, and favorable cosmetic properties. It is preferred that dental compositions be shelf stable, easy to formulate, and that they do not set so rapidly as to make them difficult to apply to a patient.

Dental compositions frequently contain monomers which are polymerized by the dentist or technician (e.g. by light, self-cure, or dual-cure). However, many dental compositions form a problematic "oxygen inhibited layer" (OIL) or "uncured layer" on their surface. This layer's polymerization is inhibited due to the presence of molecular oxygen in ambient air. As a result, incomplete polymerization occurs, causing the surface to be sticky or tacky, leading to lower hardness of the surface and/or no curing if a thin surface is present.

Several attempts have been made to provide a dental composition which cures completely and without the problematic uncured layer. Such compositions include a composition known as "Extoral," a visible-light cured dental resin formulation sold by AFR Imaging Corp. (Portland, Oreg.). Extoral cures rapidly and produces a glossy, hard (but brittle) surface upon irradiation with a normal dental curing light. While the composition of Extoral is proprietary and not publicly known, its odor belies the presence of methyl methacrylate. The strong odor is objectionable to both patients and dentists/technicians, making it difficult to use in a laboratory, and nearly impossible to use in a clinical setting.

In response, U.S. patent application Ser. No. 10/224,795 (incorporated herein by reference) relates to a dental composition lacking an oxygen inhibited layer and lacking a strong odor associated with volatile compositions. Therefore, U.S. patent application Ser. No. 10/224,795 discloses a dental composition which cures completely, and does so without the offensive odors seen in earlier compositions. Such compositions work well with halogen or other light source curing units, but do not quickly cure without an oxygen inhibited layer when exposed to dental LED light curing units. LED light units have recently become more popular due their long service time, difference in the effective spectrum emitted, and portability of the units. While the abovementioned patent application discloses the use of a dental composition with Camphorquinone ("CQ") or CQ and amine complexes or systems as a photoinitiator to produce hard curing, high gloss composition without an oxygen inhibited layer, these photoinitiators have a drawback in certain applications that has precluded their use dental compositions. More specifically, it was observed that the relatively high concentrations of CQ and amine used in the present invention with LED light curing sources to provide a no-oxygen inhibited curing created a pronounced yellowish tint in the cured resin after the resin initiator system was subjected to a curing irradiation. This is in contrast to prior art teachings of the use of CQ and CQ-amine systems at low concentrations alone or in combination with colored dyes or other photobleachable colorant compositions that lose their initial color during the curing irradiation process. See, e.g., U.S. Pat. No. 6,528,555 at Table 1 and at Col. 4, lns. 51-60, Col. 5, lns. 3-9, and Col. 8, lns. 46-50.

In order to create a CQ or CQ and amine system dental composition that quickly cures under dental LED light curing units without an oxygen inhibiting layer, the levels of CQ or CQ and amine system must be very high—thereby imparting a nearly fluorescent yellow cast to any restorations made with such a dental composition. Thus, while increased levels of CQ or CQ and amine system allow a dental composition to quickly cure under LED light curing units, and over a broader range of wavelengths, increased levels of CQ and a CQ and amine system have not been used in dental compositions due to their cosmetic deficiencies. Certainly, the use of CQ and a CQ and amine system in high quantities severely limits the application of such compositions comprising them, as extremely yellow dental restorations are cosmetically unacceptable in most applications. Therefore, an LED curable dental composition that cures without an oxygen inhibited layer and without a distinctive yellow cast would be greatly appreciated in the art.

While photobleachable dyes have been used in dental compositions in conjunction with CQ and a CQ and amine system, those systems actually add a colored dye to the composition that will disappear when a light is applied. See, e.g. U.S. Pat. No. 6,528,555 at Col. 4, 1.50-Col. 5, 1.10. Further, while the dye is photobleachable, the color imparted by the CQ or CQ and amine system remains. In short, it is known to use a complex initiator/dye system using CQ in combination with a photobleachable colorant or dye that imparts a vibrant initial color to the dental composition to assist in visualization of the application of the composition to the dental surface, wherein the dye loses some or all of this vibrant color during irradiation of the composition. This reference teaches against the use of CQ or CQ and amine initiator systems alone, and does not disclose reducing oxygen inhibition of the overall curing process through use of high concentrations of CQ or CQ and amine systems. As such, the use of photobleachable dyes fails to reduce yellowing inherent in the use of high concentrations of CQ or CQ and amine systems during their irradiation.

Therefore, it would be of great value to develop a dental composition and method that allows a dental restoration to be cured to a hard, scratch free surface without an oxygen inhibited layer, while at the same time reducing or eliminating the extreme yellow cast that is imparted through the use of CQ and amine photoinitiator system. Further, providing a composition that cures with reduced or no discoloration and/or with visible light across several different wavelengths, and which can be effectively and quickly cured without an oxygen inhibited layer using a standard dental LED light curing unit would be greatly appreciated.

SUMMARY

The present application is directed toward polymerizable dental compositions. According to one embodiment of the present application, a dental composition that cures without an oxygen inhibition layer with reduced or no noticeable unwanted yellow caste comprises a multiacrylate compound, an initiator system such as a camphorquinone and amine mixture, complex, or system, and a colorless anti-yellowing agent that visibly reduces the discoloration of the initiator when exposed to a curing irradiation. In another embodiment, the colorless anti-yellowing agent may be an iodonium ion. Further, another embodiment optionally utilizes 4-(2-hydroxy-1-tetradecycloxy)phenyl]phenyl iodonium hexafluoroantimonate; 4-octyloxyphenyl)phenyliodonium hexafluoroantimonate; or 4,4'-dimenthyl-diphenyliodonium hexafluorophosphate as the colorless anti-yellowing agent. Further optionally, the composition may include an alcohol, such as ethanol. Finally, the curing irradiation may optionally be from an LED light source, perhaps giving off light within the visible spectrum.

Another embodiment of the present application comprises a multiacrylate compound which may have at least four, at least five, or at least six functionalities per molecule, an initiator such as camphorquinone and amine, and a colorless anti-yellowing agent that visibly reduces the discoloration of the initiator when exposed to a curing irradiation. Optionally, the multiacrylate compound may be an erythritol acrylate. For example, the erythritol acrylate may be dipentaerythritol pentaacrylate, dipentaerythritol hexaacrylate, caprolactone modified dipentaerythritol pentaacrylate, or caprolactone modified dipentaerythritol hexaacrylate. Further, the composition may optionally be formulated such that it cures to form a surface lacking an oxygen inhibition layer. Further, optionally, the composition may be formulated such that it cures to lack an oxygen inhibition layer when exposed to an LED light source. In addition, the composition may optionally cure when exposed to an LED light source with an intensity of 500 mW/cm$^2$ for a specified time. For example, the specified time may be less than 50 or 30 seconds.

In addition, the compositions described above may optionally include a surfactant or a flavor, or may be formulated to have a viscosity below 100 centipoise.

Another embodiment of the present application comprises a multiacrylate compound, an initiator such as camphorquinone or a camphorquinone amine, and a colorless anti-yellowing agent that visibly reduces the discoloration of the initiator when exposed to a curing irradiation, and which further cures with a surface lacking an oxygen inhibited layer when exposed to an LED light source. Optionally, a composition may cure to a scratch free surface when exposed to an LED light source for a cure time of less than 50, less than 30, or 10 seconds. Further optionally, the composition reduces discoloration by 50% when exposed to the LED light source.

DESCRIPTION

The present application relates to polymerizable dental compositions, and more specifically to polymerizable dental compositions containing multifunctional acrylate compounds that are polymerizable by use of LED and other light sources, and cure with reduced yellowing. Embodiments and examples of these compositions and methods are discussed in turn below.

Compositions

One embodiment relates to a dental composition comprising a multiacrylate compound, an initiator, and a colorless anti-yellowing agent. The multiacrylate compound is a chemical compound comprising at least three acrylate functionalities per molecule. The composition preferably does not contain methyl methacrylate, due to its foul odor. The composition, upon curing, preferably does not form an oxygen inhibition layer, and preferably cures with reduced yellowing compared to dental compounds not employing a colorless anti-yellowing agent.

A. Initiators

As discussed above, a dental composition includes an initiator. Initiators include phosphine oxide initiators and camphorquinone ("CQ") systems, which may include amines as coinitiators or as a functional group. Examples of such initiators include 1-phenyl-1,2-propanedione (PPD), 2,4,6-trimethylbenzoyldiphenylphosphine oxide (TPO), TPO-L, Irgacure 819, Darocure 4265, camphorquinone ("CQ"), CQ and amine systems, and combinations thereof. Other initiators capable of photocleavage with or without the need for amine co-initiators have utility according to the present embodiment. The initiator can generally be present at any concentration in the composition, and typically operates to initiate polymerization of the dental composition. Examples of initiators can be found in U.S. application Ser. Nos. 10/224,795 and 11/200,924, both of which are incorporated in their entirety herein by reference.

Certain initiators, such as CQ and CQ and amine systems are known in the art to cure with the side effect of imparting substantial yellowing to the composition. However, CQ and CQ and amine systems are also known to allow initiation of polymerization with visible light, and with relatively significant depth of cure. Further, CQ and CQ and amine systems, when used in relatively high concentrations, polymerize quickly with no oxygen inhibited layer, providing a scratch-free surface. Thus, while initiators such as CQ and CQ and amine systems can be used to cure a dental composition without an oxygen inhibited layer, their application in the dental restorative area has been largely ignored in the past due to the significant discoloration they impart to restorations even after they are cured. Nonetheless, CQ and CQ and amine systems can be used without the cosmetic drawbacks when combined with a colorless anti-yellowing agent according to certain preferred embodiments of the present invention.

According to certain exemplary embodiments, concentration ranges of the initiator include about 1 weight percent of the composition or less, at least about 1 weight percent of the composition, at least about 2 weight percent of the composition, at least about 3 weight percent of the composition, at le percent of the composition ast about 4 weight percent of the composition, at least about 5 weight, at least about 6 weight percent of the composition, at least about 7 weight percent of the composition up to saturation levels of initiator in the composition, or any percentages between. It is also expected that lower concentrations can be provided in the presence of a volatile dental solvent such as acetone or ethanol that, upon evaporation, provides the desired higher effective initiator concentration in the composition. It will be appreciated that use of a CQ and amine initiator system that utilizes a conjugated or aromatic amine as a coinitiator, functional group, or additive has been shown to be more effective in creating a rapidly curing dental composition that cures without an oxygen inhibited layer than CQ and amine initiator systems that do not utilize a conjugated or aromatic amine as a coinitiator, functional group, or additive.

It will be appreciated that, in certain exemplary embodiments, where a CQ and amine initiator is used, polymerization without an oxygen-inhibited layer can be obtained by using between about 1 weight percent to about 4 weight percent of the monomer used, resulting in a fully cured polymer. It has been shown that, while higher concentrations up to saturation levels of the initiator may produce a fully cured polymer, concentrations between about 1 weight percent to about 7 weight percent of the compositions result in a fully cured polymer. In addition, other embodiments of the present invention include the use of more than one initiator. For example, the use of about 4 weight percent CQ and about 3 weight percent amine can be effectively used to create a fully cured polymer. Additional examples below show examples of various percentages used.

It will be appreciated that use of a CQ and amine initiator system composition with a dental composition, according to the present application, allows polymerization to be initiated without the need for utilizing UV radiation or light outside the visible spectrum. In addition, CQ and CQ and amine initiator systems exhibit low molar absorptivity, which allows penetration of visible light deep within a composition restoration even at low intensity levels. Further, the use of CQ or CQ and amine photoinitiator systems are particularly well-suited to initiation by LED lights used in dentistry today due to the fact that the wavelength of light emitted by current LED light curing systems correspond well to the absorption wavelengths of CQ and CQ and amine photoinitiator systems.

B. Colorless Anti-Yellowing Agent

As discussed above, a dental composition according to certain embodiments include a colorless anti-yellowing agent used to reduce the yellowing of the CQ or CQ and amine photoinitiator system. These colorless anti-yellowing agents are often cationic in nature when exposed to a curing light source, and are thought to reduce the yellow coloration of a cured dental composition by oxidizing the yellow byproducts of the composition that arise during the curing process. Colorless anti-yellowing agents include a class of compounds known as iodonium initiators. Iodonium initiators comprise a formula $R_2X^+$, where X is the cation of any halogen (X=BR, CL, F, or I), and R may be any functional group, and wherein the iodonium ion may be open-chain or cyclic in structure. Some exemplary iodonium initiators include. SarCat CD-1012 (a diaryl iodonium hexafluoroantimonate salt: [4-(2-hydroxy-1-tetradecycloxy)phenyl]phenyl iodonium hexafluoroantimonate); UV 9392C: (4-octyloxyphenyl)phenyliodonium hexafluoroantimonate; and Omnical C440: (4,4'-dimethyl-diphenyliodonium hexafluorophosphate).

According to certain exemplary embodiments, concentration ranges of the colorless anti-yellowing agents include about 1 weight percent of the composition or less, at least about 1 weight percent of the composition, at least about 2 weight percent of the composition, at least about 3 weight percent of the composition, at least about 4 weight percent of the composition, at least about 5 weight percent of the composition, at least about 6 weight percent of the composition, at least about 7 weight percent of the composition up to saturation levels of initiator in the composition, or any percentages between. It is also expected that lower concentrations can be provided in the presence of a volatile dental solvent such as acetone that, upon evaporation, provides the desired higher effective initiator concentration in the composition.

Experimentation has shown that inclusion of colorless anti-yellowing agents apparently reduce discoloration that is caused by photo-decomposition by-products of initiators occurring during the cure process, enabling the dental composition to be cured by using an LED light. Specifically, compositions comprising colorless anti-yellowing agents were mixed on white mixing paper, and irradiated with an LED light source for 5-10 seconds at intensity levels of about 500 mW/cm$^2$ to about 1000 mW/cm$^2$, and were observed to determine whether visible color reduction had taken place. For example, according to certain exemplary embodiments, concentration ranges of the colorless anti-yellowing agents include about 0.5 weight percent of the composition or less, at least about 1 weight percent of the composition, at least about 2 weight percent of the composition, up to saturation levels of colorless anti-yellowing agents in the composition, or any percentages between. Testing has shown that the presence of about 0.5 weight percent to about 2.0% by weight colorless anti-yellowing agent results in a significant whitening of the cured monomer as compared to initiator cured polymers without the use of colorless anti-yellowing agents.

This results in the ability to use compositions containing an initiator without the cosmetic difficulties typically associated with such compositions. Therefore, according to one aspect of the present application, aesthetically pleasing compositions that do not contain volatile solvents can be cured without an oxygen inhibited layer. Further, according to another aspect of the present application, the use of an initiator along with the colorless anti-yellowing agent with the composition allows an aesthetically pleasing polymer to result from curing the composition with a visible light source. For example, an LED light cure unit may be used to cure one such composition, allowing the use of battery powered light cure units to achieve a functional, aesthetically pleasing restoration.

Specifically, as discussed further in the examples below, use of colorless anti-yellowing agents allows increased levels of the CQ and conjugated or aromatic amine photoinitiator systems to be used without discoloring the cured composition to such a degree that the initiator does not display the unusable cosmetic yellowing. In some instances, the inclusion of less than 1% of a photoinitiator to a composition reduces the yellowing by half. Therefore, use of the colorless anti-yellowing agents allows cosmetically useful dental compounds to be created that cure without an oxygen inhibited layer, even when LED light curing units are used with reduced exposure times.

C. Multiacrylate Compounds

The multiacrylate compound can generally be any multiacrylate compound. Additionally, the multiacrylate compound may have at least three acrylate functionalities per molecule in relatively close spatial proximity to one another. Examples of such multiacrylate compounds include a hexafunctional aromatic urethane acrylate oligomer, a caprolactone modified dipentaerythritol hexaacrylate, dipentaerythritol pentaacrylate, di-trimethylolpropane tetraacrylate, trimethylolpropane triacrylate, and ethoxylated trimethylolpropane triacrylate. Other multiacrylate compounds comprising three acrylate functionalities per molecule, compounds comprising four acrylate functionalities per molecule, compounds comprising five acrylate functionalities per molecule, compounds comprising six acrylate functionalities per molecule, compounds comprising seven acrylate functionalities per molecule, compounds comprising eight acrylate functionalities per molecule, compounds comprising nine acrylate functionalities per molecule, and compounds comprising ten acrylate functionalities per molecule in relatively close spatial proximity to one another are also expected to have utility according to the present invention. Larger number of oligo-acrylates or polyacrylates could be added to the compositions.

The multiacrylate compound can comprise a single multiacrylate compound or a mixture of more than one multiacrylate compounds. The multiacrylate compounds can generally be present at any concentration of the composition. Example concentration ranges include at least about 20 weight percent of the composition and at least about 30 weight percent of the composition. Specific concentration examples include about 20 weight percent, about 30 weight percent, about 40 weight percent, about 50 weight percent, about 60 weight percent, about 70 weight percent, about 80 weight percent, about 90 weight percent, about 95 weight percent of the composition, and all percentages between.

Examples of specific multiacrylates can be found in U.S. application Ser. Nos. 10/224,795 and 11/200,924, both of which are incorporated in their entirety herein by reference.

D. Other Embodiments

Additional embodiments include a dental composition further comprising a co-monomer. According to one exemplary embodiment, the co-monomer polymerizes with the multiacrylate compound. The co-monomer can generally be any type of co-monomer, and preferably is a non-volatile acrylate compound with a surface tension that is similar to or higher than that of the selected multifunctional acrylate compound(s) present in the composition. Examples of co-monomers include a monoacrylate compound, diacrylate compound, a triacrylate compound, or a tetraacrylate compound. An example monoacrylate is caprolactone acrylate. Example diacrylate compounds are tripropylene glycol diacrylate, ethoxylated bisphenol A diacrylate, polyethylene glycol diacrylate, epoxy diacrylate, urethane dimethacrylate, and urethane diacrylate. An example triacrylate compound is trimethylolpropane triacrylate. An example tetraacrylate is ditrimethylolpropane tetraacrylate. According to another embodiment, Ethoxylated forms of such acrylates may be preferred due to their relatively higher surface tension.

According to another embodiment, a dental composition can further include a volatile, non-reactive solvent. Examples of such solvents include acetone, ethanol and mixtures of acetone and water, ethanol and water and/or acetone, ethanol, water, or any combination thereof.

Dental compositions can further comprise fillers, nanofillers, glass particles, or other dental materials. Examples of such fillers include Ox-50, silane-treated Ox-50, and glass ionomer powder IXG 1944 RGW from Ferro, which is also a fluoride release agent. All of these embodiments are within the scope of this disclosure.

Methods

An additional embodiment is directed towards methods of using the above-described dental compositions. A method of sealing a surface can comprise obtaining a surface; applying a composition comprising a multiacrylate compound, an initiator, and a colorless anti-yellowing agent to the surface; and curing the composition to obtain a sealed surface or restoration. The sealed surface or restoration preferably does not contain an oxygen inhibition layer.

The surface can generally be any surface to be sealed, and is presently preferred to be a dental surface, a tooth, a dental implant, an artificial tooth, a bone, a fingernail, or a toenail. Additionally, the surface may be that of a previously applied dental composition such as a dental composition.

The curing can generally be performed by any means sufficient to rapidly cure the composition. The curing step is presently preferred to comprise light curing. The light curing can be performed with visible light using an LED light curing unit commonly used in the art. The intensity of light is preferably suitable for use in a dental laboratory or in a dentist's office. Examples of light intensity ranges include about 50 mW/cm$^2$ or more, about 100 mW/cm$^2$ or more, about 200 mW/cm$^2$ or more, about 300 mW/cm$^2$ or more, about 400 mW/cm$^2$ or more, about 500 mW/cm$^2$ or more, about 600 mW/cm$^2$ or more, about 800 mW/cm$^2$ or more, and about 2000 mW/cm$^2$ or more, or any range of intensities between those levels, with it being understood that higher light intensities can also be employed.

Specific examples of light intensities include about 50 mW/cm$^2$, about 100 mW/cm$^2$, about 150 mW/cm$^2$, about 200 mW/cm$^2$, about 250 mW/cm$^2$, about 300 mW/cm$^2$, about 350 mW/cm$^2$, about 400 mW/cm$^2$, about 450 mW/cm$^2$, about 500 mW/cm$^2$, about 600 mW/cm$^2$, about 800 mW/cm$^2$, and about 2000 mW/cm$^2$. Higher light intensities may also be used. In one embodiment, visible light is used. The visible light may be of any wavelength, illustratively in the blue range (400-500 nm) or may be a mixture of various wavelengths, illustratively, white light. The intensity of light used may be chosen based on the wavelength of the light used. For example, Bisco's VIP™ Dental Light Curing system using a blue wavelength light source may be employed by the dentist. Light-curing systems for dental laboratories such as the Jeneric-Pentron Cure-Lite Plus light box system or the Triad light box system from Dentsply, Inc. may also be used for dental appliances. Bisco's ATL™ System utilizing its light source only mode, without the water environment mode, may also be used. Further, any LED curing system such as the SMARTLITE™ iQ™ LED system from Dentsply (York, Pa.) may be used to cure.

The time of light curing can generally be any time. Presently preferred time ranges include about two minutes or less, about one minute or less, less than about 30 seconds, less than about 20 seconds, less than about 15 seconds, less than about 10 seconds, and less than about 5 seconds. Specific examples of light curing times include about one minute, about 30 seconds, about 20 seconds, about 15 seconds, about 10 seconds, about 5 seconds, about 3 seconds, about 2 seconds, and about 1 second. Shorter light cure times are generally preferably to shorten patient time for the procedure and for the convenience of the dental practitioner. However, longer light cure times result in additional bleaching, and may be used to obtain the ideal shade as determined by the practitioner.

According to one embodiment, the use of light units of various wavelengths may be employed, allowing various light sources, such as LED or halogen light sources to be used.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Although the present invention has been described in considerable detail with reference to certain preferred versions thereof, other versions are possible. Therefore, the spirit and scope of the appended claims should not be limited to the description of the preferred versions contained herein.

EXAMPLES

The following are examples of some of the embodiments discussed above. It will be appreciated that these examples are offered for clarification only, and do not limit any of the embodiments to the steps, structures, or materials described.

For convenience, Table 1 lists the chemical compounds and abbreviations used throughout this specification.

TABLE 1

| Abbreviation/ product | Chemical name | Commercial source |
| --- | --- | --- |
| BZ | Benzophenone | Sartomer (Exton, PA) |
| CQ | Camphorquinone | Aldrich Chemical |
| CTXO | 2-Chlorotioxanthen-9-one | Aldrich Chemical |
| EDMAB | Ethyl (4-dimethylamino)benzoate | Esschem Company |
| MEHQ | Methylhydroquinone, a polymerization inhibitor | Aldrich Chemical |
| MMA | Methyl methacrylate | Aldrich Chemical |
| OX-50 | Fumed silicon dioxide filler | Degussa |

TABLE 1-continued

| Abbreviation/product | Chemical name | Commercial source |
|---|---|---|
| TMPTMA | Trimethylopropane trimethacrylate | Esschem Company |
| TPO | Lucirin TPO photoinitiator; 2,4,6-trimethylbenzoyldiphenylphosphine oxide | BASF (Mount Olive, NJ) |
| UDMA | Urethane dimethacrylate | Esschem |
| CD 9052 | Trifunctional acid ester | Sartomer (Exton, PA) |
| CN 120 | Epoxy diacrylate | Sartomer (Exton, PA) |
| CN 383 | Monofunctional acrylated amine coinitiator | Sartomer (Exton, PA) |
| CN 975 | Hexafunctional aromatic urethane acrylate oligomer | Sartomer (Exton, PA) |
| CN 983 | Urethane diacrylate | Sartomer (Exton, PA) |
| Kayarad DPCA20(DP20) | Caprolactone modified dipentaerythritol hexaacrylate | Sartomer (Exton, PA) |
| Kayarad DPCA60 (DP60) | Caprolactone modified dipentaerythritol hexaacrylate | Sartomer (Exton, PA) |
| SR 259 | Polyethylene glycol (200) diacrylate | Sartomer (Exton, PA) |
| SR 306 | Tripropylene glycol diacrylate | Sartomer (Exton, PA) |
| SR 344 | Polyethylene glycol (400) diacrylate | Sartomer (Exton, PA) |
| SR 349 | Ethoxylated bisphenol A diacrylate | Sartomer (Exton, PA) |
| SR 350 | Trimethylolpropane trimethacrylate | Sartomer (Exton, PA) |
| SR 351 | Trimethylolpropane triacrylate | Sartomer (Exton, PA) |
| SR 355 | Ditrimethylolpropane tetraacrylate | Sartomer (Exton, PA) |
| SR 399 | Dipentaerythritol pentaacrylate | Sartomer (Exton, PA) |
| SR 459 | Caprolactone acrylate | Sartomer (Exton, PA) |
| SR 495 | Caprolactone acrylate | Sartomer (Exton, PA) |
| SR 502 | Ethoxylated trimethylolpropane triacrylate | Sartomer (Exton, PA) |
| SR 610 | Polyethylene glycol (600) diacrylate | Sartomer (Exton, PA) |
| EtOH | Ethanol (99.5%) | Aldrich Chemical |
| C440 | IGM-C440 (4,4'-dimenthyl-diphenyliodonium hexafluorophosphate) | IGM Resins |
| UV9392C | (4-octyloxyphenyl)phenyliodonium hexafluoroantimonate | General Electric Company |

Example 1

Preparation of "No Oxygen Inhibited Layer" (NOIL) Compositions

NOIL compositions contain at least two components: a multifunctional acrylate and an initiator (such as phosphine oxide). A diluent (such as ethoxylated di- or tri-acrylate) may also be added to enhance handling of the multiacrylate and/or solubility of the initiator. The compositions can contain additional materials such as solvents, polymerizable co-monomers, inhibitors, surfactants, glass filler, fluorescent or phosphorescent compounds, dyes, colorants, fluoride compounds, and other materials used in the dental and orthodontic fields.

Example 2

Preparation of Reduced Yellow NOIL Compositions

One example of reduced yellow NOIL compositions utilizes UV9392C as the colorless anti-yellowing agent. Various examples are given in Table 2, displaying compositions that may be formed according to one embodiment. The numbers in Table 2 represent the amount of each compound in the composition by weight percent.

TABLE 2

| | Composition | | | |
|---|---|---|---|---|
| Compound | CR-1 | CR-1A | CR-3 | CR-4 |
| SR399 | 0.50 g | 0.50 g | 1.0 g | 2.00 g (with ethanol) |
| EDMAB | 20.0 mg | 20.0 mg | 20.0 mg | 35.0 mg (3%) |

TABLE 2-continued

| | Composition | | | |
|---|---|---|---|---|
| Compound | CR-1 | CR-1A | CR-3 | CR-4 |
| 1% 29 Additive | 0.1% | 0.1% | 44 mg | 100 mg (500 ppm) |
| UV9392C | 0 | 10.0 mg (4%) | 0 | 20.0 mg (2.0%) |
| CQ | 20.0 mg (4%) | 20.0 mg (4%) | 10.0 mg | 35.0 mg (3.0%) |
| EtOH | .50 g | .50 g | | |
| Reduced Coloration after Cure? | N | Y | N | Y |
| Scratch Free Surface?* | Y | Y | Y | Y |

*After irradiated for 55 @ 500 mw/cm$^2$ with a VIP light.

Light curing of CR-1 (utilizing a cross-linking resin) shows that a 4% CQ composition can be cured with an LED light utilizing an intensity of 1000 mW/cm$^2$ for a time period of 2-3 seconds results in a scratch free surface. However, the CR-1 composition cures to a yellow tone that is not aesthetically pleasing.

Light curing of CR-1A shows the addition of UV9392C to the basic composition CR-1 results in increased whitening of the cured compound. In addition, UV9392 C allows progressive bleaching of the composition by increasing irradiation time and/or light intensity. Thus, CR-1 A has the potential of allowing color matching or adjustment through irradiation time or intensity.

Light curing of CR-3 utilizing the VIP light curing system at a light intensity of 500 mW/cm$^2$ for a time period of 10 seconds resulted in a scratch free surface. Further, light curing of CR-3 utilizing the Skylight light curing system at a light intensity of 800 mW/cm$^2$-900 mW/cm$^2$ for a time period of 7 seconds resulted in a scratch free surface. Curing CR-3 using both methods resulted in discoloration higher than that seen in curing of CR-1. Further, color change (bleaching) properties were not seen to change as irradiation time changed, unlike CR-1 A.

Light curing of CR-4 utilizing the VIP light curing system at a light intensity of 500 mW/cm$^2$ for a time period of 8 seconds resulted in a scratch free surface. Further, light curing of CR-4 utilizing the Skylight light curing system at a light intensity of 1000 mW/cm$^2$ for a time period of 5 seconds resulted in a scratch free surface. Finally, CR-4 also cured to a scratch free surface when exposed to 100 mW/cm$^2$ light intensity for a period of 50 seconds. Curing the CR-4 composition using each method resulted in significant whitening of the compound, resulting in a more cosmetically pleasing cured restoration than CQ initiated compositions commonly used without colorless anti-yellowing agents, and providing bleaching results approaching and/or exceeding those seen in the CR-1 compositions. Further, color change (bleaching) properties were progressive as irradiation time and intensity increased.

Example 3

Use of Colorless Anti-Yellowing Agents

In other exemplary compositions, CD-1012, a photo initiator, was used in place of UV9392C in compositions similar to those shown in Table 2. As shown in Table 2, CD-1012 was added to dental compositions in a range from less than 2% to over 4% by weight, resulting in significant reduction of residual color after curing for 20-30 seconds with a light intensity of 400 mW/cm$^2$. In fact, testing showed that the use of 1% by weight of CD-1012 reduces the color index of some cured compositions by approximately 50%, creating a cosmetically pleasing restoration.

Example 4

Additional Examples of Photo-Inhibitor Compositions

TABLE 3

| Compound | COMPOSITION | | |
|---|---|---|---|
| | BLED-3 | BLED-3A | BLED-3B |
| SR399, % | 47.0 | 47.0 | 47.0 |
| CQ, % | 1.5 | 1.5 | 1.5 |
| EDMAB, % | 1.5 | 1.5 | 1.5 |
| CD-1012, % | 0 | 1.0 | 0.5 |
| MEHQ, ppm | 250 | 250 | 250 |
| 29 Additive | 500 | 500 | 500 |
| Ethanol | Balance | Balance | Balance |
| Scratch free[a)] | Yes | Yes | Yes |
| Discoloration[b)], ΔE * | 7.74 | 4.34 | — |

[a)]After irradiated for 5 s at 500 mw/cm$^2$ with a VIP light.
[b)]After irradiated for 20 s at 400 mw/cm$^2$ with Smartlite IQ.

In exemplary compositions, compositions were made as shown above in Table 3. Light curing of BLED-3A for 20-30 seconds with a light intensity of 400 mW/cm$^2$ resulted in a reduction of yellow by about 45%, as measured using a HunterLab™ Spectrophotometer (Ultrascan XE) when compared to the BLED-3. In particular, testing shows the shift in colors noted in Tables 3 and 4 with regard to BLED-3 vs. BLED-3A when the compositions were cured for 20-30 seconds with a light intensity of 400 mW/cm$^2$. Visual examinations showed that BLED-3A had less residual color than BLED-3B. In addition, when factoring in the effect of film thickness, 1.0% CD-1012 approximately reduced the color by about 50%.

TABLE 4

| Composition | ΔL* (Dark Shift) | Δa* (Green Shift) | Δb* (Yellow Shift) |
|---|---|---|---|
| BLED-3 | 0.66 | 2.52 | 7.28 |
| BLED-3A | 0.41 | 1.14 | 4.17 |

In Table 4 above, larger numbers indicate a greater shift in color, with higher numbers corresponding to increased color. As noted above, dental restorations are preferred to be the same color as the substrate on which it is placed. It can be seen that the BLED-3A has significantly better aesthetic qualities due to the colorless anti-yellowing agent added to 1 weight percent. Additionally, testing of the BLED-3B showed reduced yellowing over the BLED-3, but the reduction in yellowing was not as significant as that shown by BLED-3A.

TABLE 5

| Compound | Composition | | | |
|---|---|---|---|---|
| | BLED-4A1 | BLED-4A2 | BLED-4A5 | BLED-4A6 |
| BLED 4A | 1.00 g | 1.00 g | 2.00 g | 1.00 g |
| EDMAB | 10 mg | 20.0 mg | | |
| CN386 | | (4%) | 10.0 mg | 20.0 mg |
| Scratch Free Surface? | Y | Y | Y | Y |
| Reduced Coloration? | Slight | Slight | Y | Y |

In exemplary compositions, the compositions shown in Table 5 were derived from BLED-4, which comprises 9.97 g of SR399, 0.31 g of CQ, 5.0 mg MEHQ, 10.0 g of 29 ADD, and 10.50 g EtOH. In addition, BLED-4A comprises 10.00 g BLED-4, and 150 mg EDMAB. In addition, BLED-4B was formed utilizing 1.20 g. BLED-4 and 36 mg of CN386.

Light curing of the compositions with a light intensity of 450 mW/cm$^2$ resulted in the following results: all BLED-4A series resins were scratch free after seven seconds of curing, while the BLED-4B1 was still scratchable after 30 seconds. However, BLED-4B1 was nearly colorless after 30 seconds exposure, while BLED-4A, BLED-4A1, and BLED-4A2 retained much of their yellow color after 40 seconds. However, BLED-4A5 and BLED 4A6 showed significantly reduced yellowing at 40 seconds. Additional preparations utilizing C440 in place of CN386 showed that C440 can be utilized in the place of CN386, and can be used in lower concentrations to achieve similar results.

In addition to the exemplary embodiments and methods noted above, it is noted that the use of Omnical C440 resulted in increased bleaching or oxidization of a composition when combined with ethanol in the compositions. In addition, use of both Omnical C440 and CD-1012 resulted in high absorption rates over a broad range of wavelengths, with BLED-3 showing a high absorption near 400 nm. Further, a peak absorbance for compositions using both CD-1012 and Omnical C440 occurring at approximately 468 nm.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention.

For example, in addition to the above multiacrylate, initiator, inhibitor, and photoinitiator, a surfactant, such as Additive 29 ("ADD 29"), may be used to promote leveling. Illustratively, the surfactant comprises 0.01 to 1.0 percent by weight of the composition, for example 0.05 to 0.10 percent. Other components may be added, as are known in the art.

It is understood that a more pleasing composition may be obtained by adding a flavor to the composition. The flavor may be used to mask an odor or simply to provide for a more pleasant product. Illustrative flavors include essential oils such as thymol, spearmint, peppermint, eucalyptus, wintergreen, and cinnamon. Further illustratively, COE-Soft (GC America, Alsip, Ill.) may be used. A 1:1 ratio of final composition to COE-Soft results in a pleasing flavor. These and other flavors are known in the art and may be used in any of the compositions of the present invention.

What is claimed is:

1. A dental composition comprising
   a. a multiacrylate compound,
   b. an initiator system capable of initiating photopolymerization of the multiacrylate compound to form a surface lacking an oxygen inhibited layer, the initiator system comprising camphorquinone (CQ) in an amount at least about 1% by weight of the composition and an amine, and
   c. a colorless anti-yellowing agent operable to visibly reduce the discoloration of the initiator system when exposed to a curing irradiation.

2. The composition of claim 1, wherein the colorless anti-yellowing agent is an iodonium ion.

3. The composition of claim 2, wherein the colorless anti-yellowing agent is selected from the group consisting of 4-(2-hydroxy-1-tetradecycloxy)phenyl]phenyl iodonium hexafluoroantimonate; 4-octyloxyphenyl)phenyliodonium hexafluoroantimonate; and 4,4'-dimenthyl-diphenyliodonium hexafluorophosphate.

4. The composition of claim 1, further comprising an alcohol.

5. The composition of claim 4, wherein the alcohol is ethanol.

6. The composition of claim 1, wherein the curing irradiation comprises an LED light curing unit.

7. The composition of claim 6, wherein the light emitting diode (LED) light curing unit is operable to produce light within the visible spectrum.

8. The composition of claim 7, wherein the multiacrylate compound comprises four or more acrylate functionalities per molecule.

9. The composition of claim 8, wherein the erythritol acrylate is selected from the group consisting of dipentaerythritol pentaacrylate, dipentaerythritol hexaacrylate, caprolactone modified dipentaerythritol pentaacrylate, and caprolactone modified dipentaerythritol hexaacrylate.

10. The composition of claim 7, wherein the multiacrylate compound is an erythritol acrylate.

11. The composition of claim 1, wherein the initiator system comprises camphorquinone and a conjugated amine.

12. The composition of claim 11, wherein the conjugated amine is an aromatic amine.

13. The composition of claim 1, wherein the composition cures to form a surface lacking an oxygen inhibition layer and reduces the yellow coloration of the initiator system when exposed to an LED light source.

14. The composition of claim 13, wherein the composition cures to form a surface lacking an oxygen inhibition layer and reduces discoloration when exposed to an LED light source having an intensity of at least about 500 mw/cm$^2$ for a specified time.

15. The composition of claim 14, wherein the specified time is less than 50 seconds.

16. The composition of claim 14, wherein the specified time is less than 30 seconds.

17. The composition of claim 1, wherein the camphorquinone of the initiator system comprises more than about 1.5% of the composition by weight.

18. The composition of claim 1, wherein the camphorquinone of the initiator system comprises more than about 2% of the composition by weight.

19. The composition of claim 1, wherein the camphorquinone of the initiator system comprises more than about 3% of the composition by weight.

20. The composition of claim 1, further comprising a surfactant.

21. The composition of claim 1, further comprising a flavor.

22. The composition of claim 1, wherein the composition has a viscosity of below 100 centipoise.

23. A dental composition comprising
   a. a multiacrylate compound;
   b. an initiator system, the initiator system capable of initiating photopolymerization of the multiacrylate compound, the initiator system comprising at least 1% of the composition by weight camphorquinone and at least one amine;
   c. a colorless anti-yellowing agent operable to visibly reduce the yellowing of the initiator system when exposed to an LED light source; and
   d. wherein the composition forms a surface lacking an oxygen inhibition layer when exposed to an LED light source.

24. The dental composition of claim 23, wherein the composition is operable to cure to a scratch free surface when exposed to an LED light source for a cure time of less than 50 seconds.

25. The dental composition of claim 23, wherein the cure time is less than 30 seconds.

26. The dental composition of claim 23, wherein the cure time is less than 10 seconds.

27. The dental composition of claim 23, wherein the composition reduces discoloration by 50% when exposed to the LED light source.

28. A dental composition comprising:
   a. a multiacrylate compound;
   b. an initiator system comprising camphorquinone (CQ) and at least one amine, wherein the initiator system comprises at least about 1.5% of the composition; and
   c. a colorless anti-yellowing agent comprising at least approximately 0.5% of the composition.

* * * * *